US007289029B2

(12) United States Patent
Medema et al.

(10) Patent No.: US 7,289,029 B2
(45) Date of Patent: Oct. 30, 2007

(54) COMMUNICATION BETWEEN EMERGENCY MEDICAL DEVICE AND SAFETY AGENCY

(75) Inventors: Douglas K. Medema, Everett, WA (US); Daniel W. Piraino, Seattle, WA (US); Richard E Kunz, Seattle, WA (US); Richard C. Nova, Kirkland, WA (US); Cynthia P. Jayne, Redmond, WA (US)

(73) Assignee: MedTronic Physio-Control Corp., Redmond, WA (US)

( * ) Notice: Subject to any disclaimer, the term of this patent is extended or adjusted under 35 U.S.C. 154(b) by 54 days.

(21) Appl. No.: 10/335,542

(22) Filed: Dec. 31, 2002

(65) Prior Publication Data

US 2004/0124979 A1 Jul. 1, 2004

(51) Int. Cl.
*G08B 23/00* (2006.01)
(52) U.S. Cl. .............................. 340/573.1; 340/539.18; 607/5
(58) Field of Classification Search ............. 340/573.1, 340/539.18, 825.49, 825.36; 607/5, 6, 8; 434/142
See application file for complete search history.

(56) References Cited

U.S. PATENT DOCUMENTS

| 3,553,383 A | 1/1971 | Rochtus |
| 3,611,361 A | 10/1971 | Gallichote et al. |
| 3,632,879 A | 1/1972 | Freisinger |
| 3,634,846 A | 1/1972 | Fobiel |
| 3,662,111 A | 5/1972 | Rubinstein |
| 3,843,841 A | 10/1974 | Rubinstein |
| 3,883,695 A | 5/1975 | Bickel et al. |
| 3,914,692 A | 10/1975 | Seaborn, Jr. |
| 3,989,900 A | 11/1976 | Dibner |
| 4,011,409 A | 3/1977 | Conrad |
| 4,064,368 A | 12/1977 | Dibner |
| 4,102,332 A | 7/1978 | Gessman |

(Continued)

FOREIGN PATENT DOCUMENTS

EP   0 201 883 A2   11/1986

(Continued)

OTHER PUBLICATIONS

International Search Report from corresponding PCT Application Serial No. PCT/US03/40576 mailed May 4, 2005 (6 pages).

(Continued)

*Primary Examiner*—Anh V. La

(57) ABSTRACT

Techniques for initiating direct communication between an emergency medical device, such as an automated external defibrillator (AED) and a safety agency may include detecting an event and contacting the safety agency in response to the detected event and user authorization. For example, the AED may detect an event such as removal of the AED from a mount and alert an operator of the intent to send contact the safety agency. The AED determines whether an override command was received from the operator in a defined amount of time. When the operator does not input an override command, the AED interprets the absence of the override command as user authorization and contacts the safety agency via a communication unit. For instance, the AED may generate an advisory and send the advisory to the safety agency. The initiation of direct communication between the AED and the safety agency by the AED enables the operator to interact with a patient, e.g., perform CPR on the patient.

55 Claims, 6 Drawing Sheets

U.S. PATENT DOCUMENTS

| | | |
|---|---|---|
| 4,141,006 A | 2/1979 | Braxton |
| 4,259,548 A | 3/1981 | Fahey et al. |
| 4,303,801 A | 12/1981 | Anderson et al. |
| 4,338,493 A | 7/1982 | Stenhuis et al. |
| 4,417,100 A | 11/1983 | Carlson et al. |
| 4,577,182 A | 3/1986 | Millsap et al. |
| 4,635,639 A | 1/1987 | Hakala et al. |
| 4,654,640 A | 3/1987 | Carll et al. |
| RE32,856 E | 2/1989 | Millsap et al. |
| 4,829,285 A | 5/1989 | Brand et al. |
| 4,887,291 A | 12/1989 | Stillwell |
| D313,362 S | 1/1991 | Reich et al. |
| 5,012,411 A | 4/1991 | Policastro et al. |
| 5,078,134 A | 1/1992 | Heilman et al. |
| 5,131,019 A | 7/1992 | Sheffer et al. |
| 5,144,294 A | 9/1992 | Alonzi et al. |
| 5,159,317 A | 10/1992 | Brav |
| 5,173,932 A | 12/1992 | Johansson et al. |
| 5,228,449 A | 7/1993 | Christ et al. |
| 5,283,816 A | 2/1994 | Gomez Diaz |
| 5,305,370 A | 4/1994 | Kearns et al. |
| 5,319,355 A | 6/1994 | Russek |
| 5,388,144 A | 2/1995 | Nichols |
| 5,402,466 A | 3/1995 | Delahanty |
| 5,438,607 A | 8/1995 | Przygoda, Jr. et al. |
| 5,549,115 A | 8/1996 | Morgan et al. |
| 5,549,659 A | 8/1996 | Johansen et al. |
| 5,555,286 A | 9/1996 | Tendler |
| 5,566,339 A | 10/1996 | Perholtz et al. |
| 5,593,426 A | 1/1997 | Morgan et al. |
| 5,642,397 A | 6/1997 | Agbaje-Anozie |
| 5,673,304 A | 9/1997 | Connor et al. |
| 5,674,252 A | 10/1997 | Morgan et al. |
| 5,680,864 A | 10/1997 | Morgan et al. |
| 5,683,423 A | 11/1997 | Post |
| 5,683,432 A | 11/1997 | Goedeke et al. |
| 5,694,452 A | 12/1997 | Bertolet |
| 5,712,619 A | 1/1998 | Simkin |
| 5,731,757 A | 3/1998 | Layson, Jr. |
| 5,742,233 A | 4/1998 | Hoffman et al. |
| 5,745,849 A | 4/1998 | Britton |
| 5,749,902 A | 5/1998 | Olson et al. |
| 5,749,913 A | 5/1998 | Cole |
| 5,752,976 A | 5/1998 | Duffin et al. |
| 5,782,878 A * | 7/1998 | Morgan et al. ........... 607/5 |
| 5,785,043 A | 7/1998 | Cyrus et al. |
| 5,787,155 A | 7/1998 | Luna |
| 5,797,091 A | 8/1998 | Clise et al. |
| 5,835,907 A | 11/1998 | Newman |
| 5,836,993 A | 11/1998 | Cole |
| 5,838,771 A | 11/1998 | Moeller |
| 5,848,651 A | 12/1998 | McSheffrey et al. |
| 5,852,408 A | 12/1998 | Christiansen et al. |
| 5,857,966 A | 1/1999 | Clawson |
| 5,873,040 A | 2/1999 | Dunn et al. |
| 5,874,897 A | 2/1999 | Klempau et al. |
| 5,891,046 A | 4/1999 | Cyrus et al. |
| 5,891,049 A | 4/1999 | Cyrus et al. |
| 5,894,591 A | 4/1999 | Tamayo |
| 5,899,866 A | 5/1999 | Cyrus et al. |
| 5,902,234 A | 5/1999 | Webb |
| 5,914,675 A | 6/1999 | Tognazzini |
| 5,921,938 A | 7/1999 | Aoyama et al. |
| 5,926,133 A | 7/1999 | Green, Jr. |
| 5,929,777 A | 7/1999 | Reynolds |
| 5,936,529 A * | 8/1999 | Reisman et al. ......... 340/573.1 |
| 5,943,394 A | 8/1999 | Ader et al. |
| 5,951,485 A | 9/1999 | Cyrus et al. |
| 5,955,956 A * | 9/1999 | Stendahl et al. ........... 340/635 |
| 5,970,414 A | 10/1999 | Bi et al. |
| 5,987,329 A | 11/1999 | Yost et al. |
| 5,999,493 A | 12/1999 | Olson |
| 6,002,936 A | 12/1999 | Roel-Ng et al. |
| 6,006,132 A | 12/1999 | Tacker, Jr. et al. |
| 6,021,330 A | 2/2000 | Vannucci |
| 6,026,035 A | 2/2000 | Kim |
| 6,026,304 A | 2/2000 | Hilsenrath et al. |
| 6,028,514 A * | 2/2000 | Lemelson et al. ...... 340/539.13 |
| 6,041,254 A | 3/2000 | Sullivan et al. |
| 6,041,257 A | 3/2000 | MacDuff et al. |
| 6,047,207 A | 4/2000 | MacDuff et al. |
| 6,057,758 A | 5/2000 | Dempsey et al. |
| 6,083,248 A | 7/2000 | Thompson |
| 6,090,056 A | 7/2000 | Bystrom et al. |
| 6,141,584 A | 10/2000 | Rockwell et al. |
| 6,150,951 A | 11/2000 | Olejniczak |
| 6,201,992 B1 | 3/2001 | Freeman |
| 6,292,687 B1 | 9/2001 | Lowell et al. |
| 6,301,501 B1 * | 10/2001 | Cronin et al. .................. 607/5 |
| 6,301,502 B1 | 10/2001 | Owen et al. |
| 6,302,844 B1 | 10/2001 | Walker et al. |
| 6,304,780 B1 | 10/2001 | Owen et al. |
| 6,321,113 B1 | 11/2001 | Parker et al. |
| 6,334,070 B1 * | 12/2001 | Nova et al. .................... 607/5 |
| 6,351,671 B1 | 2/2002 | Myklebust et al. |
| 6,374,138 B1 | 4/2002 | Owen et al. |
| 6,398,744 B2 | 6/2002 | Bystrom et al. |
| 6,405,083 B1 | 6/2002 | Rockwell et al. |
| 6,427,083 B1 | 7/2002 | Owen et al. |
| 6,438,417 B1 | 8/2002 | Rockwell et al. |
| 6,459,933 B1 * | 10/2002 | Lurie et al. .................... 607/5 |
| 6,480,744 B2 | 11/2002 | Ferek-Petric |
| 6,493,581 B2 | 12/2002 | Russell |
| 6,527,558 B1 * | 3/2003 | Eggert et al. ............... 434/262 |
| 6,544,171 B2 * | 4/2003 | Beetz et al. ................. 600/300 |
| 6,594,634 B1 | 7/2003 | Hampton et al. |
| 6,597,948 B1 | 7/2003 | Rockwell et al. |
| 6,624,754 B1 * | 9/2003 | Hoffman et al. ......... 340/573.1 |
| 6,658,290 B1 | 12/2003 | Lin et al. |
| 6,668,192 B1 | 12/2003 | Parker et al. |
| 6,694,187 B1 | 2/2004 | Freeman |
| 6,738,671 B2 | 5/2004 | Christophersom et al. |
| 6,865,418 B2 | 3/2005 | Merry |
| 6,872,080 B2 * | 3/2005 | Pastrick et al. ............. 434/262 |
| 2001/0012955 A1 | 8/2001 | Goedeke et al. |
| 2001/0056227 A1 | 12/2001 | Gopinathan et al. |
| 2002/0038392 A1 | 3/2002 | De La Huerga |
| 2002/0103508 A1 | 8/2002 | Mathur |
| 2002/0193847 A1 | 12/2002 | Daum et al. |
| 2002/0198513 A1 | 12/2002 | Lebel et al. |
| 2003/0025602 A1 | 2/2003 | Medema et al. |
| 2003/0058097 A1 | 3/2003 | Saltzstein et al. |
| 2003/0065536 A1 | 4/2003 | Hansen et al. |
| 2003/0095648 A1 | 5/2003 | Kalb et al. |
| 2003/0109904 A1 | 6/2003 | Silver et al. |
| 2003/0120311 A1 | 6/2003 | Hansen et al. |
| 2003/0212311 A1 | 11/2003 | Nova et al. |
| 2004/0172069 A1 | 9/2004 | Hakala |

FOREIGN PATENT DOCUMENTS

| | | |
|---|---|---|
| EP | 0 801 959 A3 | 12/1998 |
| WO | WO 02/057994 A2 | 7/2002 |
| WO | WO 02/060529 A2 | 8/2002 |
| WO | WO 03/103765 A1 | 12/2003 |

OTHER PUBLICATIONS

U.S. Appl. No. 10/141,574, titled "Therapy-Delivering Portable Medical Device Capable Of Triggering And Communicating With An Alarm System", filed May 7, 2002.

* cited by examiner

US 7,289,029 B2

COMMUNICATION BETWEEN EMERGENCY MEDICAL DEVICE AND SAFETY AGENCY

TECHNICAL FIELD

The invention relates to medical devices, and more particularly, to communication between emergency medical devices and safety agencies.

BACKGROUND

Cardiac arrest is life-threatening medical condition that may be treated with external defibrillation. External defibrillation includes applying electrodes to a patient's chest and delivering an electric shock to the patient to depolarize the patient's heart and restore normal sinus rhythm. The chances that a patient's heart can be successfully defibrillated increase significantly if a defibrillation pulse is applied quickly.

In some cases, the patient's need is urgent and the patient cannot wait for trained personnel, such as paramedics, emergency medical technicians, or others trained in defibrillations techniques, to arrive. In recognition of the need for prompt treatment and the advantages of early defibrillation, automated external defibrillators (AED's) are becoming more commonplace, and are available in venues such as airports, health clubs and auditoriums.

When an AED is used to treat a patient, much of the treatment is performed by the AED rather than the person who operates the AED. In general, the AED automatically measures the patient's cardiac signals, assesses whether a shock is indicated and charges a storage element in preparation for giving the shock. When a shock is indicated, the AED may cue the operator to administer the shock, or the AED may administer the shock automatically. In addition, many AED's include visual displays, voice instructions and other audible messages that tell the operator about the status of the defibrillator. By delivering therapy in advance of arrival of emergency personnel, an AED can save a patient's life.

SUMMARY

In general, the invention is directed to techniques for initiating direct contact between an emergency medical device, such as an automated external defibrillator (AED) and a safety agency. Direct communication between the emergency medical device and the safety agency may be initiated automatically or manually in response to operator input or action taken in preparing or operating the emergency medical device. The safety agency may be, for example, an Emergency Medical System such as 9-1-1 in the United States, or a security monitoring agency.

The techniques for initiating contact with the safety agency may involve detecting an event, as described above, and contacting the safety agency in response to detecting the event and user authorization. For example, an AED may detect an event such as power-up of the AED, removal of the AED from a mount, receiving an oral command from an operator, opening of a cover associated with the AED, detecting actuation of a button or other input medium on the AED, coupling electrodes to the AED or to the patient, receiving an advisory decision to shock a patient from the AED, and delivering a shock to the patient with the AED. Contacting the safety agency may include, for example, sending an advisory, opening a voice channel, or the like.

An emergency medical device, such as an AED, may alert the operator of the intent to contact the safety agency upon detecting the event. The alert may indicate, for example, that an advisory will be sent to the safety agency in a defined amount of time unless the operator indicates otherwise. The AED may monitor for an override command to be input by the operator during the defined amount of time. The override command enables the operator to cancel the contact with the safety agency. In this manner, the AED detects user authorization, i.e., the absence of an override command, and contacts the safety agency in response to detection of an event and the user authorization.

When the AED does not detect an override command from the operator, i.e., detects user authorization, the AED contacts the safety agency. For example, the AED may generate an advisory for the safety agency. The advisory may include a variety of information such as location information, therapy information, and patient information. The advisory, for example, may include a street address indicating a location of the AED, a current electrocardiogram (ECG) measurement, and a summary of the defibrillation shocks applied to the patient.

The AED sends the advisory to the safety agency via a communication unit. The communication unit may include a network card, a wireless local area network (WLAN) card, a mobile phone, an infrared (IR) card, a modem, or any combination thereof. Alternatively, the communication unit may couple the AED and a communication device that is already coupled to a network. For example, the communication unit may electrically couple the AED to a mobile phone via a connector.

In one embodiment, the invention provides a method comprising detecting an event within an external emergency medical device and contacting a safety agency in response to the detected event and user authorization.

In another embodiment, the invention provides an external emergency medical device comprising a detector that detects an event and a communication unit that contacts a safety agency in response to the detected event and user authorization.

The invention can provide a number of advantages. In general, the invention may enable an operator of an emergency medical device, such as an AED, to initiate direct communication with a safety agency while enabling the operator to interact with a patient. For example, the operator may press a button or actuate another input medium associated with the AED to initiate a call to the safety agency.

The AED takes responsibility for placing a call to or initiating a communication session with the safety agency, which allows the operator to concentrate on placement of electrodes on the patient, performance of CPR on the patient, or provision of other therapy to the patient. In this manner, the invention can eliminate the need for the operator to leave the patient to find a phone and communicate with the safety agency.

In addition, the invention may allow an AED or other emergency medical device to automatically contact a safety agency. Automation prevents the operator from becoming preoccupied with providing therapy to the patient and delaying contact with the safety agency. In locations where automatic direct communication with the safety agency is not permitted by law, however, an override button may be present to allow the operator to cancel the communication. In this manner, the AED detects user authorization to contact the safety agency, thereby complying with applicable laws or regulations while providing added convenience to the user. In this way, the AED can promote a quick response from the safety agency.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
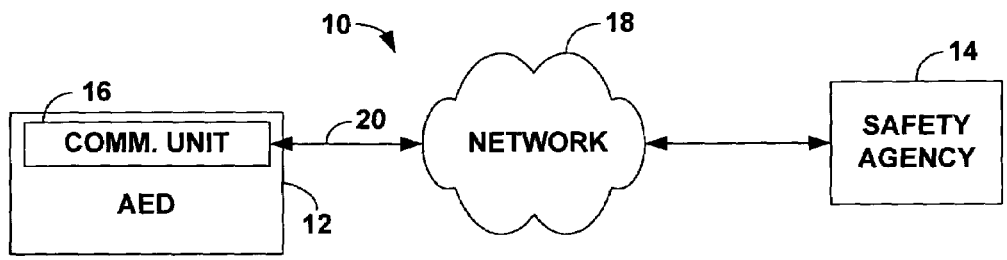
FIG. 1 is a block diagram illustrating an exemplary system in which an emergency medical device, such as an automated external defibrillator (AED), communicates directly with a safety agency in response to detecting an event.

FIGS. 1–4 illustrate a variety of communication systems providing a communication link between an emergency medical device and a safety agency. FIG. 1 is a block diagram illustrating an exemplary system 10 in which an emergency medical device, such as an automated external defibrillator (AED) 12, communicates directly with a safety agency 14 in response to detecting an event and user authorization. Direct communication between AED 12 and safety agency 14 may be initiated automatically. Alternatively, direct communication between AED 12 and safety agency 14 may be initiated manually in response to operator input or action taken in preparing or operating the AED. Safety agency 14 may be, for example, an Emergency Medical System such as 9-1-1 in the United States, or a security monitoring agency.

As shown in FIG. 1, AED 12 includes a communication unit 16 that is coupled to a network 18 via at least one link 20. More than one link 20 may couple communication unit 16 to network 18 in order to provide alternative communication paths between safety agency 14 and AED 12 in case one link 20 fails. Communication unit 16 may include a network card, a wireless local area network (WLAN) card, a mobile phone, an infrared (IR) card, a modem, or any combination thereof. Communication unit 16 may instead couple AED 12 and a communication device that is already coupled to network 18. For example, communication unit 16 may electrically couple AED 12 to a mobile phone via a connector that connects to the mobile phone and AED 12. Further, communication unit 16 may electrically couple AED 12 via Bluetooth or other wireless medium.

Network 18 may be a combination of network architectures, including a public switched telephone network (PSTN), an integrated services digital network (ISDN), an Internet protocol (IP) network, a local area network (LAN), a wide area network (WAN), a wireless communications network, or an asynchronous transfer mode (ATM) network. Link 20 may be a wireless link, a wired link, optical links or the like.

AED 12 detects an event and contacts safety agency 14 in response to the detected event and user authorization. User authorization may be the absence of an override command once contact is initiated. For example, AED 12 may open a voice channel or send an advisory to safety agency 14 upon detection of an event and user authorization. In this manner, AED 12 initiates direct communication between AED 12 and safety agency 14. The communication may serve to request that emergency personnel be dispatched to the scene of the emergency. To that end, the communication may include location information, as well as patient information, therapy information, or other pertinent information. The event detected by AED 12 may include power-up of AED 12, removal of AED 12 from a mount, receiving an oral command from an operator, opening of a cover associated with AED 12, detecting actuation of a button or other input medium on AED 12, coupling electrodes to AED 12 or to the patient, receiving an advisory decision to shock a patient from AED 12, and delivering a shock to the patient with AED 12. Accordingly, by detection of one or more of such events, AED 12 may respond automatically to set up a communication link for communication with safety agency 14.

Direct communication between AED 12 and safety agency 14 may advantageously reduce the amount of time before delivery of early advanced care to the patient. For example, initiation of communication by AED 12 may avoid delay in delivery of therapy by the first responder, who might otherwise be occupied with locating a telephone and placing a call to a safety agency 14. In addition, in some embodiments, directly contacting safety agency 14 may eliminate the need to contact a third party, such as a security agency, which then contacts safety agency 14. Directly contacting safety agency 14 with the external emergency medical device enables the operator to interact with the patient while concurrently advising safety agency 14 of the situation. For example, the operator may place electrodes on the patient or perform CPR or other therapy to the patient. In emergency situations, such as a cardiac arrest of a patient, time is of the essence.

Figure 2:
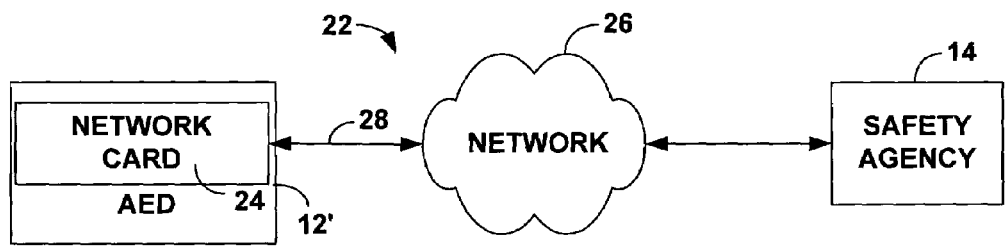
FIG. 2 is a block diagram illustrating an exemplary AED that includes a network card for communicating directly with a safety agency.

FIG. 2 is a block diagram illustrating an exemplary system 22 in which an AED 12' communicates directly with a safety agency 14 in response to detecting an event. AED 12' includes a network card 24 that communicates data, voice, video, and the like with a network 26 via at least one network link 28. Network card 24 and network 26 may communicate in accordance with communication protocols such as Transmission Control Protocol/Internet Protocol (TCP/IP), Frame Relay protocol, Asynchronous Transfer Mode (ATM) protocol, or other communication protocols. Network card 24 may be coupled to network link 28 via an interface port (not shown).

AED 12' may, for example, send an advisory to safety agency 14 via network card 24 in response to detecting an event. The advisory may take the form of a data packet and may include information such as location information, patient information, therapy information, or the like. For example, the advisory may include a street address associated with AED 12' and measurement data, such as an electrocardiogram (ECG), obtained by AED 12'. Routing devices (not shown), such as routers, switches, and the like, within network 26 relay the packet through network 26 to safety agency 14. In this manner, AED 12' initiates direct communication between AED 12' and safety agency 14.

In response to receiving the advisory, safety agency 14 may deploy the necessary emergency personnel, such as emergency medical technicians (EMTs), paramedics, and the like. Further, safety agency 14 may communicate with an operator of AED 12'. For example, a dispatcher within safety agency 14 may provide instructions to the operator, such as how to perform CPR. AED 12' may receive the instructions from safety agency 14 and convey the instructions to the operator, e.g., via a voice or text interface.

Figure 3:
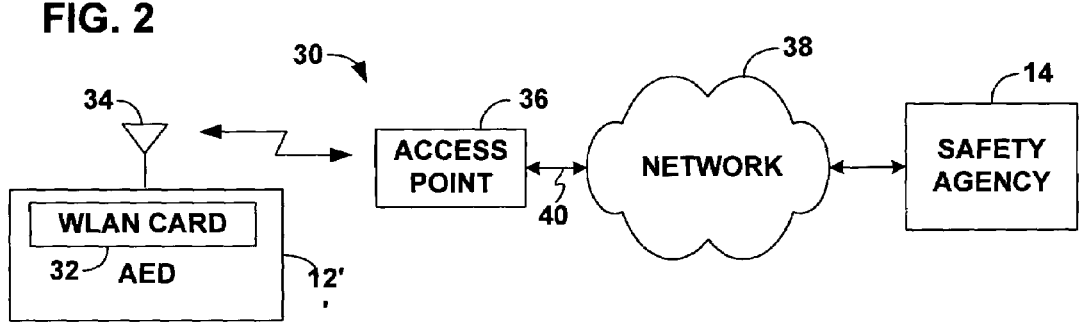
FIG. 3 is a block diagram illustrating another exemplary AED that includes a wireless local area network (WLAN) card for communicating directly with a safety agency.

FIG. 3 is a block diagram illustrating another exemplary system 30 in which an AED 12" communicates directly with a safety agency 14 in response to detecting an event. AED 12" includes a wireless local area network (WLAN) card 32 and at least one antenna 34. Antenna 34 may be embedded within WLAN card 32 or coupled to WLAN card 32 via a connector. AED 12" may include more than one antenna 34 arranged to pick up different strengths of signals and use the strongest of the signals, i.e., arranged for antenna diversity. Arranging the antenna signals in different configurations may create spatial diversity, polarization diversity, frequency diversity, or a combination thereof.

System 30 includes at least one wireless access point 36 coupled to a network 38 via a link 40. Wireless access point 36 permits wireless communication between network 38 and AED 12". Wireless access point 36 may integrate a hub, a switch or a router (not shown) to serve AED 12". WLAN card 32, antenna 34 and wireless access point 36 may be used to communicate data, voice, video and the like between AED 12" and network 38 according to a variety of different wireless transmission techniques, such as Orthogonal Frequency Division Multiplexing (OFDM). Link 40 may be an Ethernet or other network connection.

AED 12" detects an event and contacts safety agency 14 in response to detecting the event. More particularly, AED 12" may transmit an advisory to wireless access point 36 via WLAN card 32 and antenna 34. Wireless access point 36 and routing devices (not shown) within network 38 relay the advisory to safety agency 14. In this manner, AED 12" communicates directly with safety agency 14 advantageously saving time as well as enabling an operator to interact act with a patient. As mentioned above, AED 12" may also receive information from safety agency 14 and convey the information to the operator.

Figure 4:
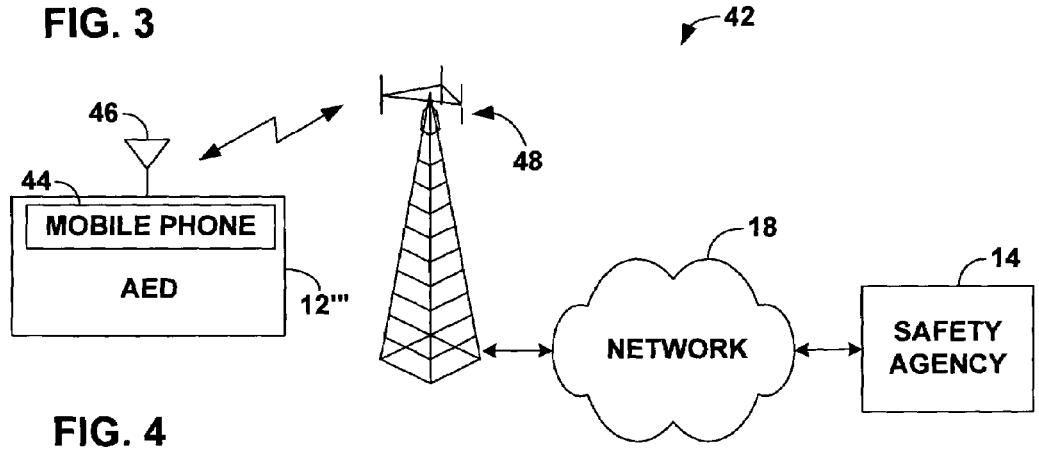
FIG. 4 is a block diagram illustrating another exemplary AED that includes a mobile phone for communicating directly with a safety agency.

FIG. 4 is a block diagram illustrating another exemplary system 42 in which an AED 12''' communicates directly with a safety agency 14 in response to detecting an event. AED 12''' includes a mobile phone 44 and at least one antenna 46. Antenna 46 may be integrated within mobile phone 44 or may be a separate entity. Although mobile phone 44 is shown within AED 12''' in FIG. 4, mobile phone 44 may be electrically coupled to AED 12''' via a connector. The connector may be a cable that links mobile phone 44 to AED 12''' or a mount to accept mobile phone 44.

AED 12''' contacts safety agency 14 in response to detecting an event. In particular, mobile phone 44 transmits a signal, which may include an advisory, to a base station 48 via antenna 46. Alternatively, mobile phone 44 may open a voice channel between safety agency 14 and AED 12'''. Mobile phone 44 and base station 48 may communicate according to wireless techniques such as code division multiple access (CDMA), time division multiple access (TDMA), frequency division multiple access (FDMA) or some other modulation and multiple access techniques. Base station 48 may be coupled to a network 49. Base station 48 relays the signal to network 49, which in turn relays the signal to safety agency 14. In this manner, AED 12" communicates directly with safety agency 14. As mentioned above, AED 12" may also receive communications from safety agency 14 and convey the information contained in those communications to the operator.

Figure 5:
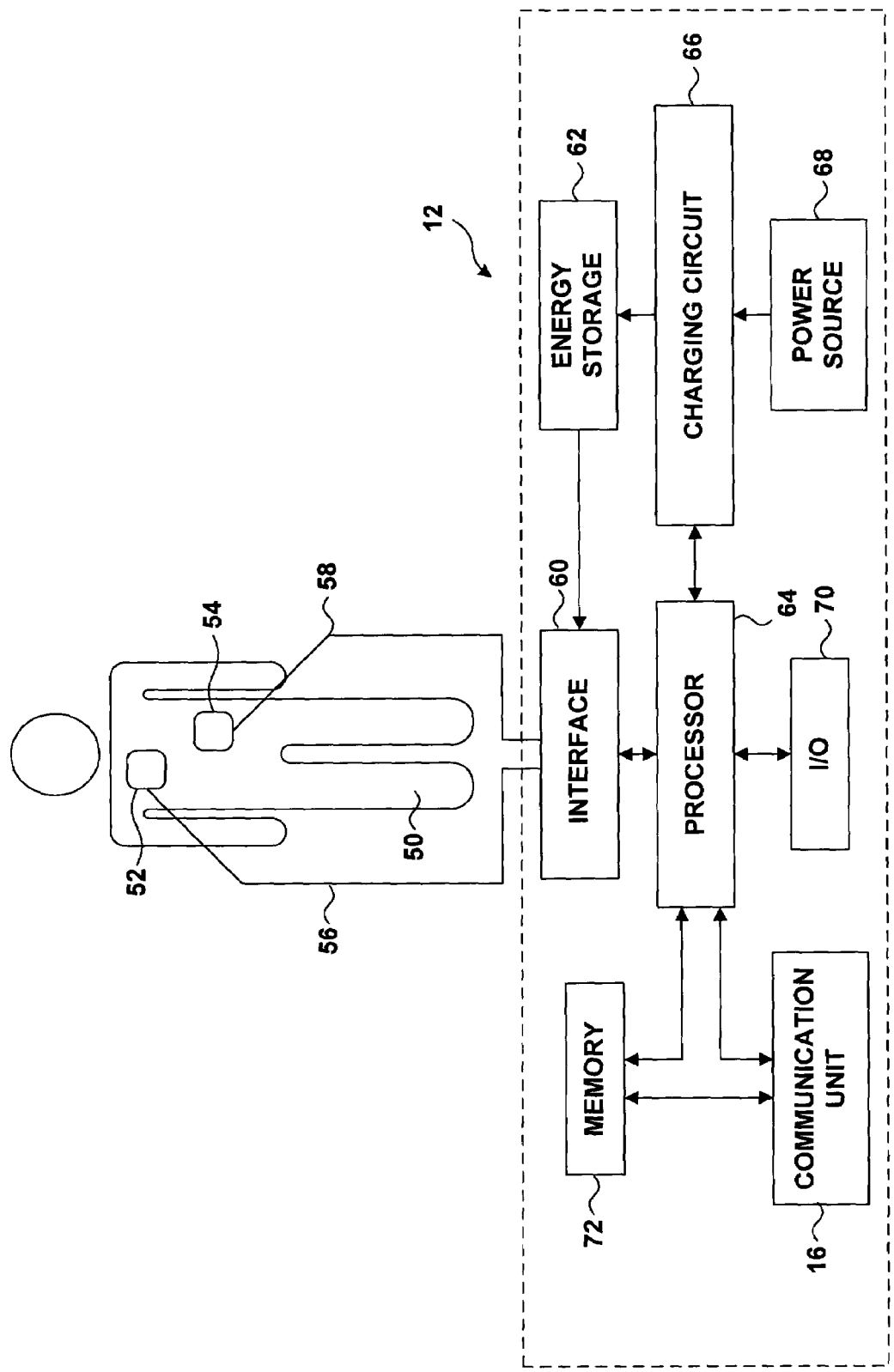
FIG. 5 is a block diagram showing a patient coupled to an AED.

FIG. 5 is a block diagram showing a patient 50 coupled to an exemplary AED 12. Although the invention may be applicable to a variety of external emergency medical devices, various embodiments will be described herein in the context of defibrillators. AED 12 administers defibrillation therapy to patient 50 via electrodes 52 and 54, which may be hand-held electrode paddles or adhesive electrode pads placed on the skin of patient 50. The body of patient 50 provides an electrical path between electrodes 52 and 54.

Electrodes 52 and 54 are coupled to AED 12 via conductors 56 and 58 and interface 60. In a typical application, interface 60 includes a receptacle (not shown), and connectors 56, 58 plug into the receptacle. Electrical impulses or signals may be sensed by AED 12 via electrodes 52 and 54 and interface 60. Electrical impulses or signals may also be delivered from AED 12 to patient 50 via electrodes 52 and 54 and interface 60.

Interface 60 includes a switch (not shown) that, when activated, couples an energy storage device 62 to electrodes 52 and 54. Energy storage device 62 stores the energy for a dosage of energy or current to be delivered to patient 50. The switch may be of conventional design and may be formed, for example, of electrically operated relays. Alternatively, the switch may comprise an arrangement of solid-state devices such as silicon-controlled rectifiers or insulated gate bipolar transistors.

Energy storage device 62 includes components, such as one or more capacitors (not shown), that store the energy to be delivered to patient 50 via electrodes 52 and 54. Before a defibrillation pulse may be delivered to patient 50, energy storage device 62 must be charged. A processor 64 directs a charging circuit 66 to charge energy storage device 62 to a high voltage level. Charging circuit 66 comprises, for example, a flyback charger that transfers energy from a power source 68 to energy storage device 62. Because the life of patient 50 may depend upon receiving defibrillation, charging should take place rapidly so that the defibrillation shock may be delivered with little delay.

When the energy stored in energy storage device 62 reaches the desired level, AED 12 is ready to deliver the defibrillation shock. The shock may be delivered automatically or manually. When the shock is delivered automatically, processor 64 activates an input/output (I/O) device 70, which may be a microphone (input) and a speaker (output), that warns the operator that AED 12 is ready to deliver a defibrillation shock to patient 50. The warning informs the operator of the impending shock so that no one other than patient 50 will receive the defibrillation shock. Processor 64 then activates the switch to electrically connect energy storage device 62 to electrodes 52 and 54, and thereby deliver a defibrillation shock to patient 50. In the case of a manual delivery, processor 64 may activate an I/O device 70 that informs the operator that AED 12 is ready to deliver a defibrillation shock to patient 50. The operator may activate the switch by manual operation, such as pressing a button, and thereby deliver a defibrillation shock to patient 50.

Processor 64 may perform other functions as well, such as monitoring electrocardiogram (ECG) signals sensed via electrodes 52 and 54 and received via interface 60. Processor 64 may determine whether patient 50 suffers from a condition that requires a defibrillation shock, based upon the ECG signals. In addition, processor 64 may also evaluate the efficacy of an administered defibrillation shock, determine whether an additional shock is warranted, and the magnitude of energy to be delivered in the additional shock.

Power source 68 may comprise, for example, batteries and/or an adapter to an exterior power source such as an electrical outlet. In addition to supplying energy to charging circuit 66 and energy storage device 62, power source 68 also supplies power to components such as processor 64 and I/O device 70, e.g., via a power supply circuit (not shown).

A memory 72 may store data, such as vital signs of patient 50 and a history of the therapy delivered to patient 50. In addition, memory 72 may store instructions that direct the operation of processor 64. Further, memory 72 may store information regarding the location of AED 12, a prescribing physician associated with AED 12, or other information associated with that particular AED 12. Memory 72 may include volatile storage, such as random access memory, and/or non-volatile storage, such as flash memory or a hard disk.

A communication unit 16 allows AED 12 to contact a safety agency 14 in response to detecting an event. Communication unit 16 may, for example, send an advisory to safety agency 14 or open a voice channel between safety agency 14 and AED 12. As described above, communication unit 16 may include a network card, a wireless local area network (WLAN) card, a mobile phone, an infrared (IR) card, or any combination thereof. The advisory conveys to safety agency 14 location information of patient 50, patient information, therapy information, and the like. Communication unit 16 may further receive information from safety agency 14 and convey the information to the operator via I/O device 70.

Figure 6:
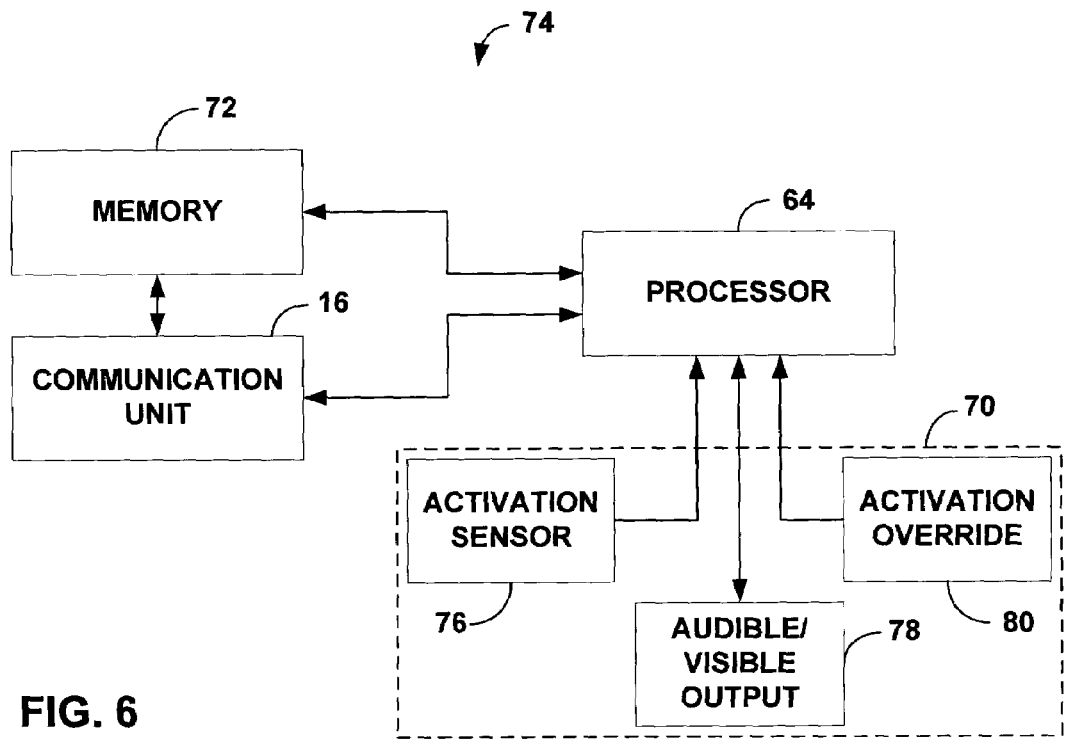
FIG. 6 is a block diagram illustrating an exemplary embodiment of communications circuitry within an AED for automatic initiation of direct communication between the AED and a safety agency.

FIG. 6 is a block diagram illustrating an exemplary embodiment of communications circuitry 74 within an AED 12 for automatic initiation of direct communication between AED 12 and a safety agency 14. As shown in FIG. 6, communications circuitry 74 includes an activation detector 76 that detects an event, such as removal of AED 12 from a mount, power up of AED 12, coupling electrodes to AED 12 or to the patient, receiving an advisory decision to shock a patient from AED 12, and delivering a shock to the patient with AED 12. For example, activation detector 76 may be an accelerometer that detects movement of AED 12, i.e., detects when AED 12 is removed from a mount. Activation detector 76 may further be a mechanical switch or some other type of sensor besides an accelerometer.

Activation detector 76 communicates to a processor 64 that the event was detected. Processor 64 conveys to the operator, via an audible/visible output 78 of the intent to contact safety agency 14. For example, processor 64 may convey to the operator that an advisory will be sent to safety agency 14. Audible/visible output 78 may be a speaker, a display, or a combination thereof. Processor 64 may wait for a defined time interval before contacting safety agency 14. The operator may choose to cancel the contact within the defined time interval via an activation override 80. The operator may choose to cancel the contact with safety agency 14, for example, when the event is detected in a non-emergency situation. For example, an operator may power-up the AED to train a new operator in which case the operator would not want to send an advisory to safety agency 14. Activation override 80 may, for example, be a button, switch, dial or other input medium that, when actuated by the operator, cancels the advisory. Alternatively, activation override 80 may take the form of an audible command from the operator. For example, the operator may simply speak a command, such as "cancel contact," into a microphone. Activation detector 76, audible/visible output 78 and activation override 80 may be included within I/O device 70.

When the operator does not cancel the contact within the defined time interval, absence of the override is interpreted as user authorization. In response, processor 64 may access memory 72 to generate an advisory. Memory 72 may include location information, such as a recorded message indicating the location of AED 12. Further, memory 72 may contain patient information and therapy information. Processor 64 may, for example, generate an advisory from a subset of the information stored in memory 72, and send the advisory to safety agency 14 via a communication unit 16.

Figure 7:
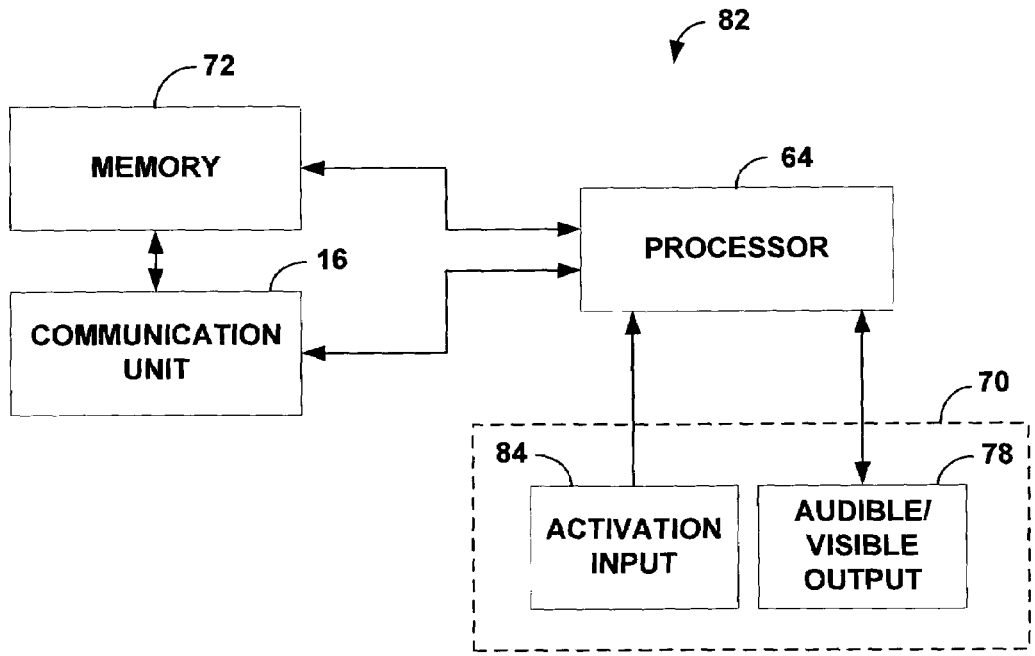
FIG. 7 is a block diagram illustrating another exemplary embodiment of communications circuitry within an AED for operator initiation of direct communication between the AED and a safety agency.

FIG. 7 is a block diagram illustrating another exemplary embodiment of communications circuitry 82 within an AED 12 for operator initiation of direct communication between AED 12 and a safety agency 14. Communications circuitry 82 conforms substantially to communications circuitry 74 illustrated in FIG. 6, but incorporates an activation input 84 instead of an activation detector 76 and activation override 80.

Activation input 84 may be a button, switch, dial or other input medium that an operator may actuate in order to initiate direct contact between AED 12 and safety agency 14. Activation input 84 and audible/visible output 78 might be included within I/O device 70. Because the operator initiates the direct communication between AED 12 and safety agency 14, no override is necessary. Upon actuation of the button, processor 64 may contact safety agency 14. In one embodiment of the invention, processor 64 generates an advisory that includes a subset of information from a memory 72, and sends the advisory to safety agency 14 via a communication unit 16. Alternatively, processor 64 may open a voice channel between AED 12 and safety agency 14 via communication unit 16.

Figure 8:
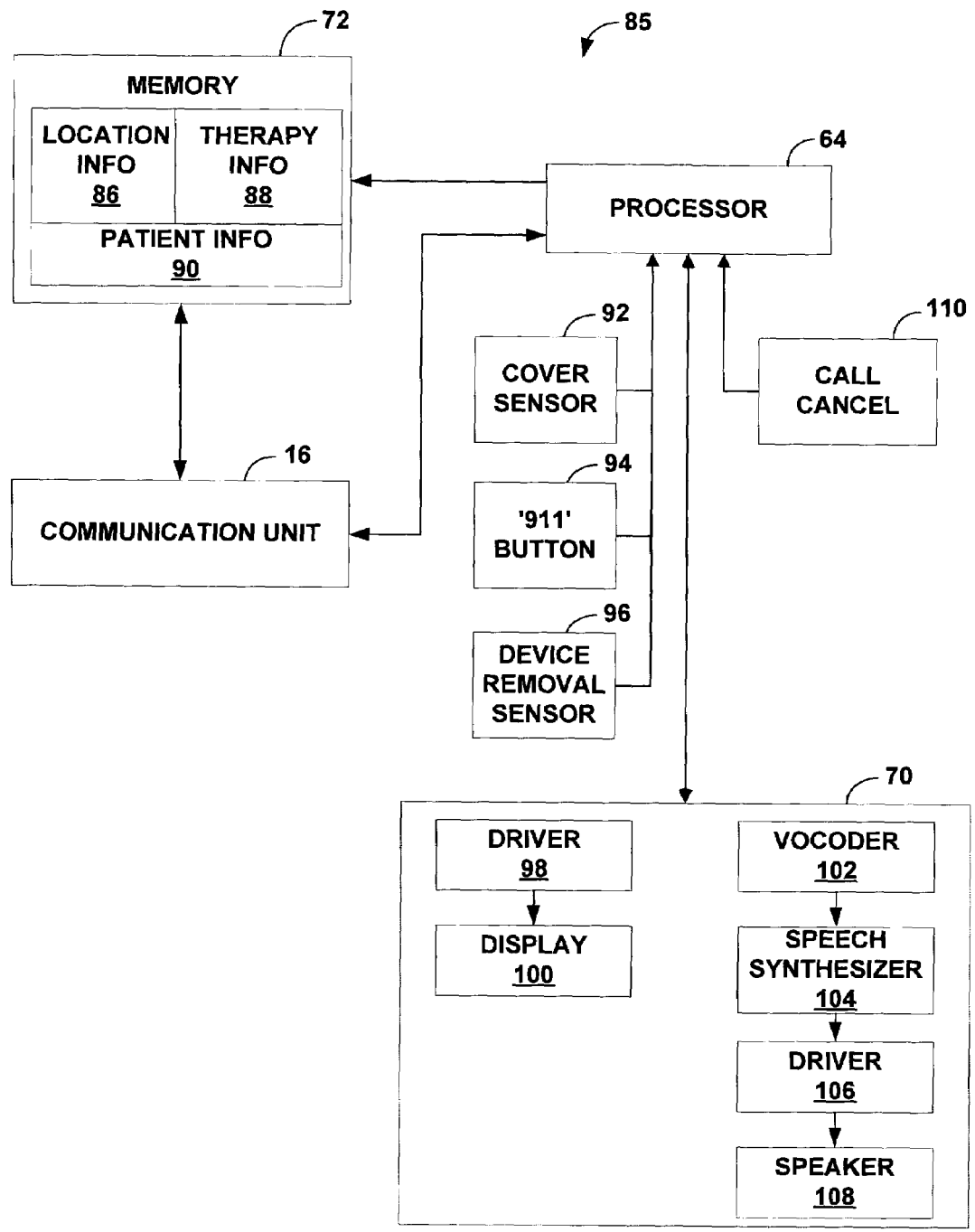
FIG. 8 is a block diagram illustrating communications circuitry within an AED in further detail.

FIG. 8 is a block diagram illustrating communications circuitry within an AED 12 in further detail. Communications circuitry 85 includes a cover sensor 92 that detects when the cover of AED 12 is opened and a device removal sensor 96 that detects when the device is removed from a mount. Both cover sensor 92 and device removal sensor 96 may be considered activation detectors. AED 12 further includes an actuation input. Specifically, in the example of FIG. 8, AED 12 includes a '911' button 94 that an operator may press to initiate direct contact with a safety agency 14.

AED 12 may detect an event using cover sensor 92 or device removal sensor 96 and notify the operator of the intent to contact a safety agency 14 in a defined amount of time. A processor 46 may convey a notification message to the operator via an I/O device 70. I/O device 70 may convey the message to the operator via a driver 98 and a display 100. Alternatively, I/O device 70 may convey an audible message to the operator using a vocoder 102, a speech synthesizer 104, a driver 106, and a speaker 108.

An activation override, such as call cancel button 110, may allow the operator to cancel the contact with safety agency 14. Call cancel button 110 may be a touch screen button or a physical button mounted on AED 12. Upon actuation of call cancel button 110 AED 12 cancels the contact with safety agency 14.

Upon no actuation of call cancel button 110 or upon actuation of '911' button 94, AED 12 perceives user authorization and contacts safety agency 14. For example, processor 46 may retrieve information, such as location information 86, therapy information 88, and patient information 90, from memory 72 and generate an advisory message. Location information 86 may include an address associated with AED 12 or a prescribing physician associated with AED 12 of that location. Therapy information 88 may include the number of shocks administered to a patient, the amount of energy per shock, and any information regarding other therapies administered to the patient. Patient information 90 may include patient data measured by electrodes 52, 54 including an ECG signal, a heart rate, and any information calculated from measurements such as determination of ventricular fibrillation or the like. AED 12 sends the advisory to safety agency 14 via communication unit 16.

Figure 9:
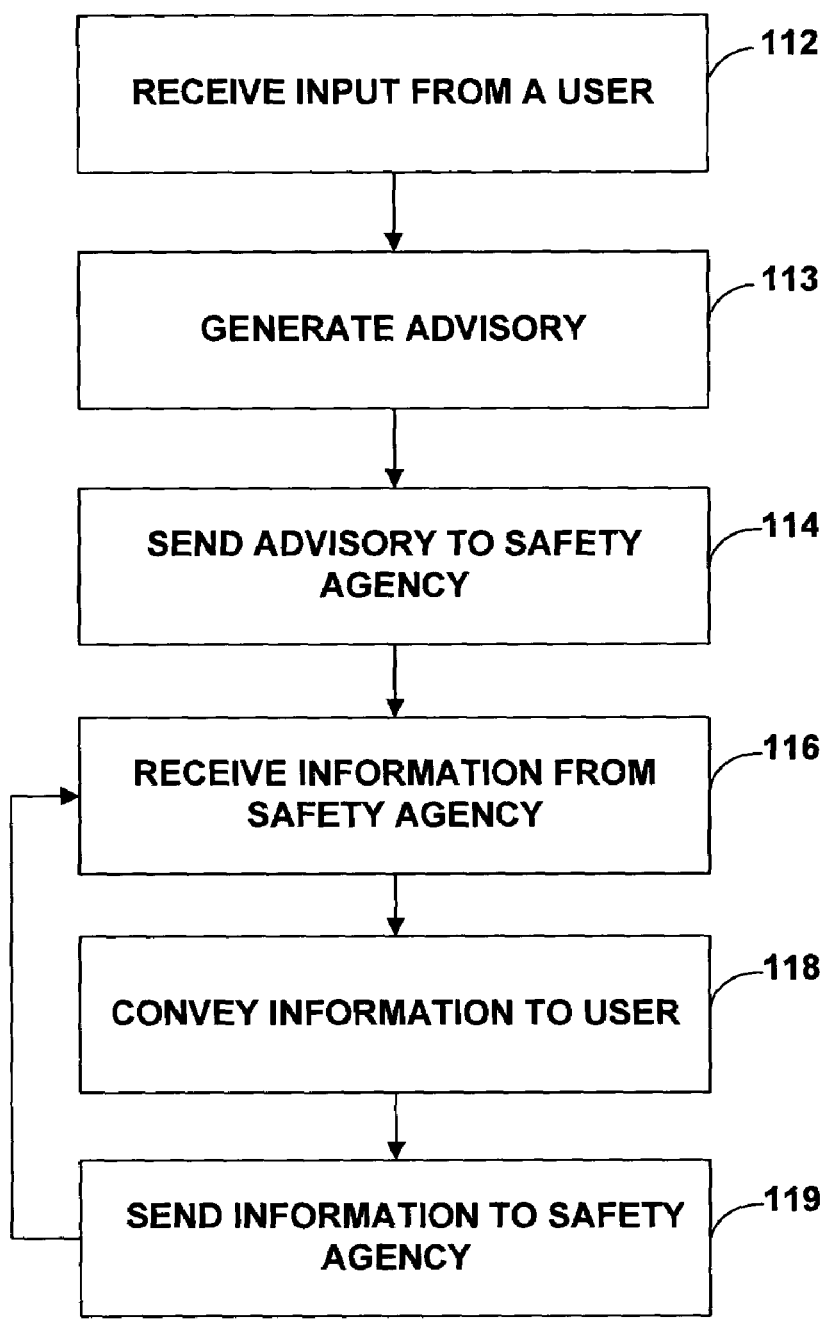
FIG. 9 is a flow diagram illustrating an AED communicating directly with a safety agency in response to receiving input from an operator.

FIG. 9 is a flow diagram illustrating an AED 12 communicating directly with a safety agency 14 in response to receiving input from an operator. The flow diagram of FIG. 9 is for purposes of example. In operation, AED 12 may contact safety agency 14 via sending an advisory, opening a voice channel, or the like. AED 12 receives input from an operator to initiate communication with the safety agency 14 (112). The input from the operator may be an actuation of a button, such as a '911' button 94. Alternatively, the input from the operator may be a command from the operator to contact the safety agency. The command from the operator may be an oral command into a microphone or a command input via a keyboard, touch screen, or other input device.

AED 12 generates an advisory upon receiving input from the operator (113). Processor 64 may retrieve information stored in memory 54, such as location information 66, therapy information 68, and patient information 70 and generate the advisory with a subset of the information. The information contained in the advisory may depend on when AED 12 receives the input from the operator. For example, when the input from the operator is received before any patient data is measured or therapy is delivered, the advisory may contain only location information, such as a street address indicating a location of AED 12. In the case in which only location information is included in the advisory, the advisory may be a recorded message stored in memory 72. The message may be recorded upon installation of AED 12 at a particular site. However, when the input from the operator is received after patient data is measured and therapy is delivered, the advisory may contain more detailed information. For instance, the advisory may include a street address indicating a location of AED 12, a current electrocardiogram (ECG) measurement, and a summary of the defibrillation shocks applied to the patient.

AED 12 sends the advisory to safety agency 14 via communication unit 16 (114). As described above, communication unit 16 may include one or more of a network card 24, WLAN card 32, a mobile phone 44, or an IR card. In the case in which communication unit 16 is a mobile phone 44, communication unit 16 may, for example, place a call to safety agency 14 via base station 48. Communication unit 16 enables the operator to interact with the patient while contacting safety agency 14. For example, the operator may place electrodes on the patient or perform CPR on the patient.

AED 12 may further receive communications from safety agency 14 (116). For example, a dispatcher may provide instructions to the operator. AED 12 may convey the instructions to the operator visually via a display 80 or orally via a speaker 88 (118). Speaker 88 used to convey the instructions to the operator may further be used to output standard voice prompts. In this case, there may be interference between the standard voice prompts of AED 12 and communications from safety agency 14. AED 12 may be configured to route the standard voice prompts to the dispatcher of safety agency 14 when communications between safety agency 14 and the operator are in session. The dispatcher may then relay the instructions to the operator. Alternatively, the operator may communicate with safety agency 14 via a first microphone and first speaker and standard voice prompts may be output via a second speaker.

AED 12 may periodically send information to safety agency 14 (119). AED 12 may, for example, send updated therapy information upon a new defibrillation shock being administered to the patient. In another example, the operator may reply to the dispatcher's instructions with a question or with an indication that the instructions have been performed. The response from the operator may be a text response input into AED 12 via an input device, such as a keyboard. Alternatively, the response may be an oral response into a microphone. In this manner, the dispatcher and the operator may maintain a conversation as if communicating via a phone.

Figure 10:
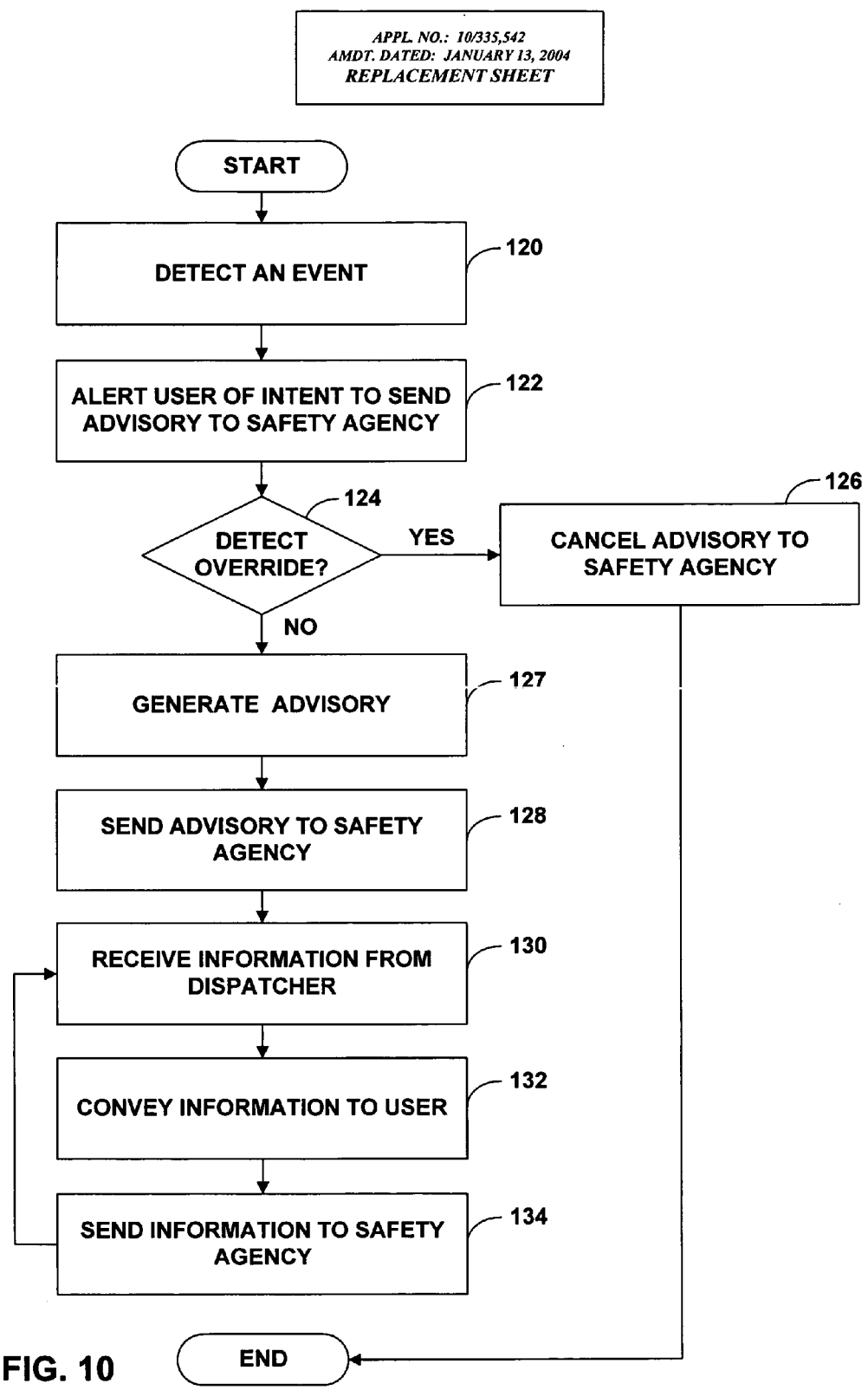
FIG. 10 is a flow diagram illustrating an AED communicating directly with a safety agency automatically in response to detecting an event.

FIG. 10 is a flow diagram illustrating an AED 12 automatically initiating direct communication with a safety agency 14 in response to detecting an event. The flow diagram of FIG. 10 is for purposes of example. In operation, AED 12 may contact safety agency 14 via sending an advisory, opening a voice channel, or the like. Automation prevents the operator from becoming preoccupied with providing therapy to the patient and delaying contact with the safety agency. AED 12 detects an event (120). Again, the event detected may be power-up of AED 12, removal of AED 12 from a mount, opening of a cover associated with AED 12, coupling electrodes to AED 12 or to the patient, receiving an advisory decision to shock a patient from AED 12, and delivering a shock to the patient with AED 12. The event may be detected using a detector, such as a sensor, within the circuitry of AED 12. Alternatively, the detector may be external to AED 12, such as a sensor on one of the electrodes 52, 54 placed on the patient.

AED 12 may alert the operator of the intent to send an advisory to safety agency 14 (122). The alert to the operator may be displayed on a display 80 or may be prompted via a speaker 88. The alert may indicate, for example, that an advisory will be sent to safety agency 14 in a defined amount of time unless the operator indicates otherwise. AED 12 monitors for an override command to be input by the operator during the defined amount of time (124). In locations where automatic direct communication with the safety agency is not permitted by law, an override button, switch, dial, or other input medium may be present to allow the user to input an override command to cancel the advisory and thereby permit user intervention to authorize or deauthorize the communication of an advisory. The override command may be input by the operator via a keyboard, a touch screen, a microphone, or any other input device. When AED 12 detects an override command from the operator, AED 12 cancels the advisory to safety agency 14 (126). In this manner, AED 12 may be configured to comply with applicable laws or regulations that may not permit direct, automated contact with a safety agency. In particular, the override command inserts the user into the process of contacting the safety agency, while permitting automated initiation and setup of the communication.

When AED does not detect an override command from the operator, AED 12 perceives user authorization and generates an advisory (127). Processor 64 may retrieve information stored in memory 54, such as location information 66, therapy information 68, and patient information 70 and generate the advisory with a subset of the information. The information contained in the advisory may depend on when AED 12 detects the event. For example, when the event detected is power-up of AED 12, the advisory may include only location information, such as a street address indicating a location of AED 12. However, when the detected event is an event such as application of a defibrillation shock to the patient, the advisory may contain more detailed information including patient data measurements and therapy information.

AED 12 sends the advisory to safety agency 14 via communication unit 16 (128). AED 12 may further receive communications from safety agency 14 (130). For example, a dispatcher may provide instructions to the operator. AED 12 may convey the instructions to the operator via a display 80 or a speaker 88 (132). AED 12 may periodically send information, such as updated patient information to safety agency 14 (134). Further, as described above operator may respond to the dispatcher.

Various embodiments of the invention have been described. These and other embodiments are within the scope of the following claims. These embodiments are illustrative of the practice of the invention. Various modifications may be made without departing from the scope of the claims. The techniques of the invention may be applied to other external emergency medical devices such as external therapeutic medical devices and external diagnostic medical devices. These and other embodiments are within the scope of the following claims.

The invention claimed is:

1. A method comprising:
   detecting an event within an external therapeutic emergency medical device;
   alerting a user of an intent to contact a safety agency in response to the detected event;
   determining that the user authorized contacting the safety agency in response to the alert; and
   contacting the safety agency in response to the determination.

2. The method of claim 1, in which detecting an event includes detecting removal of the device from a mount.

3. The method of claim 1, in which detecting an event includes detecting opening of a cover associated with the medical device.

4. The method of claim 1, in which detecting an event includes detecting power-up of the medical device.

5. The method of claim 1, in which detecting an event includes detecting an oral command from an operator.

6. The method of claim 1, in which detecting an event includes detecting actuation of an input medium on the medical device.

7. The method of claim 6, in which the input medium is one of a button, a switch, and a dial.

8. The method of claim 1, in which the emergency medical device includes an automated external defibrillator (AED).

9. The method of claim 8, in which detecting an event includes detecting coupling of electrodes to the AED.

10. The method of claim 8, in which detecting an event includes detecting attachment of electrodes to a body of a patient.

11. The method of claim 8, in which detecting an event includes receiving an advisory decision to shock a patient from the AED.

12. The method of claim 8, in which detecting an event includes delivering a shock to the patient with the AED.

13. The method of claim 1, further comprising conveying information to the safety agency.

14. The method of claim 1, in which contacting the safety agency includes opening a voice channel between the device and the safety agency.

15. The method of claim 1, in which contacting the safety agency includes sending an advisory from the device to the safety agency.

16. The method of claim 15, in which the advisory includes a recorded message.

17. The method of claim 15, in which the advisory includes at least one of patient information, therapy information, and location information.

18. The method of claim 1, in which determining that the user authorized contacting the safety agency comprises determining that an override command was not received by the emergency medical device in response to the alerting of the user.

19. The method of claim 1, further comprising:
   receiving instructions from a dispatcher of the safety agency; and
   conveying the instructions to an operator.

20. The method of claim 18, in which conveying the instructions to the operator includes conveying the instructions to the operator via a speaker.

21. The method of claim 18, in which conveying the instructions to the operator includes conveying the instructions to the operator via a display.

22. The method of claim 1, further comprising contacting the safety agency using one of a mobile phone, a wireless local area network (WLAN) card, a infrared (IR) card, a network card, and a modem.

23. The method of claim 15, wherein sending an advisory comprises sending a prerecorded message stored by the external therapeutic emergency medical device that includes information relating to a location of the external therapeutic emergency medical device.

24. The method of claim 1, wherein determining that the user authorized contacting the safety agency comprises receiving an authorization input from a user in response to the alert.

25. An external therapeutic emergency medical device comprising:
   a detector that detects an event and alerts a user of an intent to contact a safety agency in response to the detected event; and
   a communication unit that contacts a the safety agency in response to a determination that the user authorized contacting the safety agency in response to the alert.

26. The device of claim 25, in which the communication unit contacts the safety agency by sending an advisory from the device to the safety agency.

27. The device of claim 25, in which the communication unit contacts the safety agency by opening a voice channel between the device and the safety agency.

28. The device of claim 25, in which the event is removal of the device from a mount.

29. The device of claim 25, in which the event is opening of a cover associated with the device.

30. The device of claim 25, in which the event is power-up of the device.

31. The device of claim 25, in which the event is actuation of an input medium on the device.

32. The device of claim 31, in which the input medium is one of a button, a switch, and a dial.

33. The device of claim 25, further comprising an input medium to initiate the detection.

34. The device of claim 33, in which the input medium is one of a button, a switch, and a dial.

35. The device of claim 25, in which the communication unit contacts the safety agency in response to a determination that an override command was not received by the emergency medical device in response to the alerting of the user.

36. The device of claim 25, further comprising a memory to store information.

37. The device of claim 36, wherein the information stored in memory includes at least one of location information, patient information, and therapy information.

38. The device of claim 25, further comprising a speaker to convey information to an operator.

39. The device of claim 25, further comprising a display to convey information to an operator.

40. The device of claim 25, further comprising a microphone to input information into the device.

41. The device of claim 25, in which the communication unit includes at least one of a mobile phone, a wireless local area network (WLAN) card, a infrared (IR) card, a network card, and a modem.

42. The device of claim 25, in which the device includes an automated external defibrillator (AED).

43. The device of claim 25, further comprising a memory to store a prerecorded message that includes information relating to a location of the external therapeutic emergency medical device, wherein a communication unit sends the message to the safety agency in response to the detected event and user authorization.

44. The device of claim 25, wherein the communication unit contacts the safety agency in response to receiving an authorization input from the user in response to the alert.

45. An external therapeutic emergency medical device comprising:
   means for detecting an event within the emergency medical device;
   means for alerting a user of an intent to contact a safety agency in response to the detected event;
   means for determining that the user authorized contacting the safety agency in response to the alert; and
   means for contacting the safety agency in response to the determination.

46. The device of claim 45, in which the means for detecting an event detects removal of the device from a mount.

47. The device of claim 45, in which the means for detecting an event detects opening of a cover associated with the medical device.

48. The device of claim 45, in which the means for detecting an event detects power-up of the medical device.

49. The device of claim 45, in which the means for detecting an event detects an oral command from an operator.

50. The device of claim 45, in which the means for detecting an event detects actuation of an input medium on the medical device.

51. The device of claim 45, in which the input medium is one of a button, a switch, and a dial.

52. The device of claim 45, in which the device includes an automated external defibrillator (AED).

53. The device of claim 45, in which the means for determining that the user authorized contacting the safety agency comprises means for determining that an override command was not received by the emergency medical device in response to the alerting of the user.

54. The device of claim 45, wherein the means for determining that the user authorized contacting the safety agency comprises means for receiving an authorization input from the user in response to the alert.

55. An external therapeutic emergency medical device comprising:
   a detector that detects an event;
   a communication unit; and
   a processor that alerts a user of an intent to contact a safety agency in response to the detected event, determines that the user authorized contacting the safety agency after the alert, and controls the communication unit to contact the safety agency in response to the determination.

* * * * *

UNITED STATES PATENT AND TRADEMARK OFFICE
CERTIFICATE OF CORRECTION

PATENT NO. : 7,289,029 B2
APPLICATION NO. : 10/335542
DATED : October 30, 2007
INVENTOR(S) : Medema et al.

It is certified that error appears in the above-identified patent and that said Letters Patent is hereby corrected as shown below:

In column 1, line 13, before "life-threatening" insert -- a --.

In column 12, line 57, in Claim 25, before "the" delete "a".

Signed and Sealed this

Seventeenth Day of November, 2009

David J. Kappos
*Director of the United States Patent and Trademark Office*